US008207388B2

(12) United States Patent
Bencini et al.

(10) Patent No.: US 8,207,388 B2
(45) Date of Patent: Jun. 26, 2012

(54) CATALYTIC COMPOSITION AND PROCESS FOR THE TRANSALKYLATION OF AROMATIC HYDROCARBONS

(75) Inventors: Elena Bencini, Virgilio-Mantova (IT); Gianni Girotti, Novara (IT)

(73) Assignee: Polimeri Europa S.p.A., Brindisi (IT)

( * ) Notice: Subject to any disclaimer, the term of this patent is extended or adjusted under 35 U.S.C. 154(b) by 1 day.

(21) Appl. No.: 10/538,641

(22) PCT Filed: Dec. 15, 2003

(86) PCT No.: PCT/EP03/14519
§ 371 (c)(1),
(2), (4) Date: Nov. 9, 2005

(87) PCT Pub. No.: WO2004/056475
PCT Pub. Date: Jul. 8, 2004

(65) Prior Publication Data
US 2006/0258893 A1    Nov. 16, 2006

(30) Foreign Application Priority Data
Dec. 20, 2002   (IT) ................. MI2002A2712

(51) Int. Cl.
*C07C 15/12*    (2006.01)
*B01J 29/06*    (2006.01)
*B01J 29/08*    (2006.01)

(52) U.S. Cl. ........ 585/475; 585/319; 585/323; 585/448; 585/467; 585/470; 502/63; 502/64; 502/79; 252/455 Z; 252/477 R

(58) Field of Classification Search ............. 585/323, 585/475, 319, 448, 467, 470; 502/63, 64, 502/79; 252/455 Z, 477 R
See application file for complete search history.

(56) References Cited

U.S. PATENT DOCUMENTS

| | | | | | |
|---|---|---|---|---|---|
| 3,848,012 | A | * | 11/1974 | Applegrath et al. | 585/449 |
| 4,185,040 | A | * | 1/1980 | Ward et al. | 502/64 |
| 4,459,426 | A | * | 7/1984 | Inwood et al. | 585/323 |
| 5,302,769 | A | | 4/1994 | Marler et al. | |
| 5,750,814 | A | * | 5/1998 | Grootjans et al. | 585/323 |

FOREIGN PATENT DOCUMENTS
EP    0 847 802    6/1998

* cited by examiner

*Primary Examiner* — Prem C Singh
(74) *Attorney, Agent, or Firm* — Oblon, Spivak, McClelland, Maier & Neustadt, L.L.P.

(57) ABSTRACT

A catalytic composition is described for the transalkylation of aromatic hydrocarbons comprising a zeolite and an inorganic binder, characterized by an extra-zeolitic porosity, i.e. the porosity obtained by adding the mesoporosity and the macroporosity fractions present in the catalytic composition, higher than or equal to 0.7 cc/g, which is such as to consist for a fraction of at least 30% of pores having a diameter greater than 100 nanometers. These catalytic compositions have a crushing strength not lower than 1.7 kg/mm and an apparent density not higher than 0.5 g/cc. A process is also described for the transalkylation of polyalkylated aromatic hydrocarbons which uses these catalytic compositions.

40 Claims, 6 Drawing Sheets

PSD obtained with Hg porosimetry

PSD obtained with $N_2$ absorption

Total extra-zeolitic PSD

Fraction > 100nm

CATALYTIC COMPOSITION AND PROCESS FOR THE TRANSALKYLATION OF AROMATIC HYDROCARBONS

The present invention relates to catalytic compositions comprising a zeolite and an inorganic binder, characterized by particular mechanical and porosity characteristics, suitable for being used as catalysts in industrial fixed-bed reactors.

In order to be used in industrial fixed-bed reactors, zeolitic materials must be contained in catalysts consisting of the zeolite itself and an inorganic binder, suitably prepared. Said preparation, in fact, gives to the catalyst new mechanical characteristics, compared to the starting raw materials, which are necessary for avoiding its breakage and consequent production of fine powder during loading, running and discharge operations of the industrial reactor.

The resulting catalysts should also have extra-zeolitic porosity characteristics such as to limit to the minimum the resistance to the mass transfer of reactants and products from the outside to the inside of the catalyst and vice versa. The extra-zeolitic porosity characteristics, and in particular its absolute value and the percentage distribution of said porosity in relation to the pore dimensions, represent a fundamental aspect for catalyst performances. In addition to the role of these aspects on the catalyst performances, the effect of the catalyst particle size must also be considered: resistance to the diffusion of reactants and products inside the porous structure of the catalyst proves to be higher with an increase in the size of the catalyst particles.

With respect to the catalytic performances, it is preferable, in the case, for example, of catalysts in pellet form, to have a dimension as reduced as possible, which, however, for evident reasons, causes a decrease in the mechanical characteristics of the catalyst, in particular its crushing strength. The mechanical characteristics of the catalyst, moreover, are further reduced with an increase in the extra-zeolitic porosity.

It can therefore be asserted that, up until now, the improvement in the diffusion properties of a catalyst was obtained to the detriment of the mechanical characteristics, as the former are positively influenced by an increase in the extra-zeolitic porosity and by a decrease in the diameter of the catalyst particle, while the second ones are otherwise negatively influenced by an increase in the extra-zeolitic porosity and by a decrease in the diameter of the catalyst particle.

U.S. Pat. No. 5,118,896, for example, describes the preparation of a catalyst, starting from a zeolite and an inorganic binder in powder form, characterized by an extra-zeolitic porosity whose fraction with a pore radius having dimensions higher than 450 Å is equal to 0.25-0.50 cc/g and with a diameter of the catalyst particle $\leq \frac{1}{32}$ inch (equal to about 0.8 mm).

U.S. Pat. No. 4,169,111 describes a process for the production of ethyl benzene characterized in that part of the diethyl benzenes produced in the alkylation section are recycled to the alkylation section itself whereas the remaining part of diethyl benzenes and triethyl benzenes is sent to the transalkylation section and wherein, in both the alkylation and transalkylation sections, a catalyst based on zeolite, preferably zeolite Y, and an inorganic binder is used together with an inorganic binder. The catalyst used in both sections is prepared in the form of extrudates in order to provide the necessary mechanical characteristics, so as to have a ratio between the outside surface and the catalyst particle volume preferably within the range of 85-160 $inch^{-1}$ and has pores with a radius ranging from 150 to 500 Å, the latter however having no role and likewise, no role being attributed to the total pore volume or pore volume fraction with a radius ranging from 150 to 500 Å, which are not even described. With respect to the high ratios between the outside surface and volume of catalysts formed, also obtained be resorting to particular geometries such as dilobate, tri-lobate cylinders or other curved forms, it is known that they provide better properties in the diffusion of reactants and products inside the mass of the catalytic bed, and not inside the catalyst particle, with a consequent modest improvement in the overall performances of the reactors in which said catalysts are used.

U.S. Pat. No. 5,182,242 describes the preparation of a catalyst consisting of a zeolite and an inorganic binder characterized by a low acidity. A metal-polymer is used as additive in the preparation, which, as a result of the calcination, is eliminated, leaving as residue the inorganic constituent part in the form of an oxide. All oxides of groups IVA and IVB, as well as mixtures of oxides such as silica/alumina, silica/magnesia, silica/zirconia and silica/titania are suitable as inorganic binder components of the catalyst.

EP 847802 describes the preparation of a catalyst based on beta zeolite and an inorganic binder characterized by a particular extra-zeolitic porosity, i.e. the porosity obtained by summing the mesopore and macropore fraction. The catalyst described did, in fact, have a fraction equal to at least 25% of said extra-zeolitic porosity consisting of pores having a radius higher than 100 Å and a pore volume, still referring to the extra-zeolitic porosity alone, of not less than 0.8 cc/g. The crushing strength of the catalyst particle indicated in Example 4 of EP 847802 (catalyst A1) proves to be equal to 1.3 kg/mm.

Figure 1:
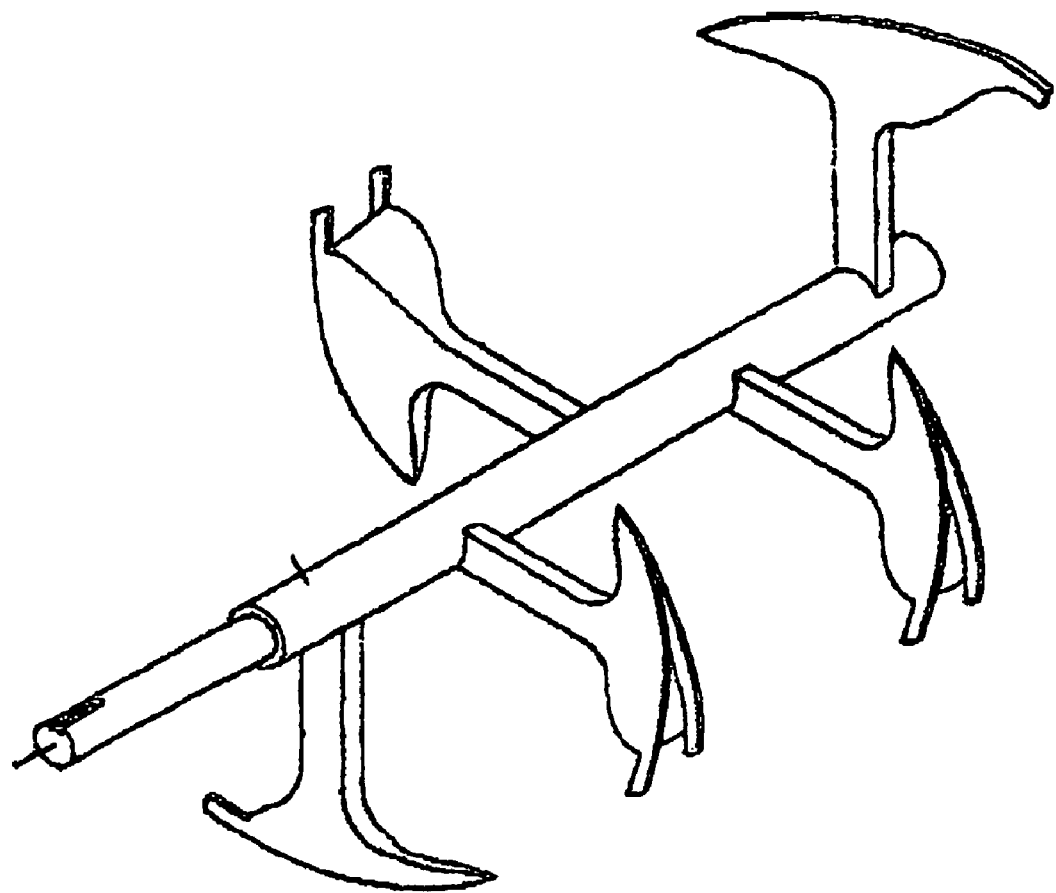
FIG. 1 shows the ploughs of a high speed mixer used in a process of the invention.

The Applicant has now found a zeolitic catalyst with particular porosity characteristics which are such as to guarantee particularly high catalytic performances in terms of duration and consequently productivity, and at the same time with excellent mechanical characteristics, such as crushing strength and resistance to abrasion.

An object of the present invention therefore relates to a catalytic composition comprising a zeolite having a crystalline structure with openings consisting of 12 tetrahedrons, i.e. belonging to the group of large-pore zeolites, and γ-alumina as inorganic binder, said composition being characterized by a pore volume, obtained by adding the mesoporosity and macroporosity fractions present in the catalytic composition itself, greater than or equal to 0.7 cc/g, wherein at least 30% of said volume consists of pores with a diameter greater than 100 nanometers.

The sum of the mesoporosity and macroporosity fractions present in the catalytic composition is hereunder indicated as extra-zeolitic porosity, whereas the microporosity fraction present in the catalytic composition, which is due to the contribution of the zeolite alone, is indicated as zeolitic porosity.

The terms microporosity, mesoporosity or transitional porosity and macroporosity are used herein in accordance with the Dubinin classification provided in Introduction to Powder Surface Area, Wiley-Interscience publication, authors Lowell and Seymour, chapter 10, page 80 (1979) and correspond to the following porosity ranges:

macroporosity: porosity referring to pores with a radius >1000 Å (diameter 200 nanometers)

mesoporosity: porosity referring to pores with a radius ranging from 1000 Å (diameter 200 nanometers) to 15 Å (diameter 3 nanometers)

microporosity: porosity referring to pores with a radius <15 Å (diameter 3 nanometers)

The zeolite contained in the catalytic composition of the present invention is selected from the group of large-pore zeolites and can, for example, be beta zeolite, zeolite Y or zeolite ZSM-12. Beta zeolite is described in U.S. Pat. No. 3,308,069, zeolite ZSM-12 is described in U.S. Pat. No. 3,832,449.

According to a preferred aspect of the present invention, the zeolites contained in the catalytic composition of the present invention are in acidic form, i.e. in the form in which most of the cationic sites are occupied by hydrogen ions.

The catalytic compositions containing zeolite Y in acidic form represent a preferred aspect of the present invention. Zeolite Y is described in U.S. Pat. No. 3,130,007. The preparation of zeolite Y is described in "Verified Synthesis of Zeolitic Materials" H. Robson Editor, Elsevier, second revised edition 2001, whereas the post-synthesis treatments to which zeolite Y can be subjected are described in "Introduction to Zeolite Science and Practice" chapter 5, H. van Bekkum and al. Editors, Studies in Surface Science and Catalysis, Vol. 58, Elsevier.

Zeolites Y having a $SiO_2/Al_2O_3$ molar ratio ranging from 10 to 20, more preferably ranging from 11 to 17, i.e. zeolites Y obtained through de-alumination post-synthesis treatments, are preferably used in the compositions of the present invention. The metal content in the zeolite, expressed as oxides, is lower than or equal to 1000 ppm by weight.

The catalytic compositions of the present invention, and in particular those containing zeolite Y, have a crushing strength of the catalyst particle equal to or higher than 1.7 kg/mm (crushing strength/length of the catalyst particle).

The compositions of the present invention, and in particular those containing zeolite Y, have a particularly low apparent density, not higher than 0.5 g/cc and a catalytic particle diameter in extruded form of not less than 1.8 mm. Preferably the catalytic particle diameter is higher than or equal to 2.0 mm. The catalyst of the present invention is preferably in the form of regular cylindrical pellets.

The catalysts of the present invention are prepared starting from the zeolite and an inorganic compound precursor of γ-alumina. Catalytic compositions prepared starting from zeolite Y and an inorganic compound precursor of γ-alumina are a preferred aspect of the present invention. Aluminas in the form of bohemite or pseudo-bohemite, with a metal content, expressed as oxides, lower than or equal to 1000 ppm can be used as precursor.

The relative weight ratio zeolite/binder in the catalytic composition is higher than 1:1 and lower than or equal to 4:1.

The preparation process of the materials according to the present invention comprises:

a) preparing a mixture including a zeolite in acidic form belonging to the class of large-pore zeolites, preferably zeolite Y, and a precursor of the binder selected from bohemite and pseudo-bohemite, by means of mechanic mixing of the components, using a high speed mixer, at a revolution speed of between 900 and 1100 rpm, for not less than 50 minutes;

b) slowly adding to said mixture, constantly under stirring, a solution at a concentration not higher than 0.5% by weight of an acid and demineralized water, in such a quantity as to have a final ratio between the acid weight and total weight of the mixture prepared in step a) of between 0.25 and 0.50%;

c) submitting the mixture obtained in the previous step b) to an extrusion forming process;

d) submitting the product obtained in step c) to drying in a ventilated oven, at a temperature not higher than 30° C., for not less than 48 hours;

e) submitting the product obtained in step d) to an air calcination process starting from room temperature up to temperatures not lower than 550° C. and not higher than 600° C. for an overall calcination time of not less than 30 hours.

In the mixture prepared in step a), the zeolite, preferably zeolite Y, is mixed with the binder precursor in such a quantity as to obtain, on the basis of the weight loss of the individual components at 550° C. previously measured, a relative weight quantity zeolite/binder in the final catalyst higher than 1:1 and lower than or equal to 4:1.

In step b), the mixing which the mixture undergoes during the addition of the acid, is effected at a much lower rate than that at which step a) is carried out, for example ranging from 200 to 600 rpm. The acid used in step b) can be selected, for example, from acetic acid, nitric acid and oxalic acid, preferably acetic acid.

At the end of the acid addition, the resulting mixture can be subjected to further mixing, the rate being maintained constant.

The extrusion in step c) is carried out according to the known techniques. It is possible to use extrusion machines of the gear press extruder type, single screw extruder, double turning screw extruder. A gear press extruder is preferably used.

The specific properties relating to the extra-zeolitic porosity and to the mechanical characteristics of the catalytic composition, object of the present invention, are due to the particular preparation procedure of the catalyst.

The catalytic compositions of the present invention can be suitably used in transalkylation processes of aromatic hydrocarbons with polyalkylated aromatic hydrocarbons, particularly of benzene with diethyl benzene and possibly triethyl benzene, to give ethyl benzene. Compositions containing zeolite Y are preferably used.

The transalkylation reaction of polyalkylated aromatic hydrocarbons is of primary industrial interest and, in particular, is currently used for the recovery of polyethyl benzenes in industrial plants for the production of ethyl benzene. The general design of an industrial plant for the production of ethyl benzene includes a main alkylation reaction section, in which ethylene and benzene are reacted to produce ethyl benzene in the presence of a catalyst of the acidic type, preferably a catalyst containing a zeolite. In this reaction, in spite of the high selectivity now reached by the new generation of zeolitic catalysts used for the purpose, significantly high quantities of by-products are formed however, especially polyethyl benzenes, due to the subsequent polyalkylation reactions of benzene with ethylene. In industrial production plants of ethyl benzene based on the use of zeolite-based catalysts, there is consequently, together with the main reaction section, a secondary transalkylation reaction section in which the polyethyl benzenes, mainly diethyl benzenes and triethyl benzenes (recoverable by-products), are recovered by reaction with benzene to give ethyl benzene.

In the two alkylation and transalkylation reaction sections, another series of by-products are also formed, in addition to the recoverable by-products, in overall quantities which are lower than that of the recoverable by-products, which form the sum of the unrecoverable impurities and by-products.

The main unrecoverable impurities and by-products formed both in the alkylation and transalkylation reaction mainly consist of low molecular weight products such as oligomers of ethylene and xylenes (the latter mainly formed in the alkylation section), the group of biphenyl ethanes (1,1 biphenyl ethane, ethyl-1,1 biphenyl ethane, diethyl-1,1 biphenyl ethane, 1,2 biphenyl ethane, ethyl-1,2 biphenyl ethane, diethyl-1,2 biphenyl ethane) and the group of higher polyethyl benzenes (tetraethyl benzenes, pentamethyl benzenes and hexa-ethyl benzenes).

The group of low molecular weight impurities, as already mentioned, cannot be recovered. The impurities belonging to the group of biphenyl ethanes cannot be recovered by means of transalkylation reaction with benzene whereas although the remaining impurities belonging to the group of higher polyethyl benzenes, can in principle be recovered by means of transalkylation reaction with benzene to give ethyl benzene, in practice they are unrecoverable, due to the extreme difficulty in separating them by distillation from the impurities belonging to the group of biphenyl ethanes.

In an industrial plant for the production of ethyl benzene, the sum of all the unrecoverable impurities and by-products therefore represents a direct measurement of the increase in consumption of the benzene and ethylene reactants with respect to their stoichiometric quantity necessary for the sole production of ethyl benzene.

The sum of all the non-recoverable impurities, with the exception of the low molecular weight impurities previously specified, is normally indicated with the term Flux oil. The overall quantity of Flux oil produced in modern production plants of ethyl benzene based on the use of the new generation of zeolite-based catalysts can vary in relation to the reaction conditions and type of zeolitic catalyst used in the two reaction sections.

It is known however that regardless of the type of zeolitic catalyst used in the two reaction sections and in spite of the fact that the highest quantity of ethyl benzene is produced in the alkylation section and only a minority amount is produced in the transalkylation section, most of the unrecoverable by-products come from the transalkylation section (Alkylation of Aromatics with Ethylene and Propylene: Recent Developments in Commercial Processes. Applied Catalysis A: General 221 (2001) 283-294). The reasons for this mainly lie in the different selectivity to unrecoverable impurities and by-products which characterizes the two reaction steps, generally lower in the alkylation step and normally higher in the transalkylation step.

The transalkylation reaction of polyethyl benzenes (diethyl benzenes and triethyl benzenes) is, in fact, a less advantageous reaction with respect to the alkylation reaction, both with respect to the kinetics and thermodynamics and consequently requires higher operating temperatures which correspond to lower selectivities. The conversion of polyethyl benzenes per passage in the transalkylation section is in fact limited by the thermodynamic equilibrium, causing a significant recycling quantity of the latter with a consequent increase in the incidence of secondary reactions forming unrecoverable impurities and by-products in this section.

Another aspect which makes the transalkylation step particularly critical with respect to yield and overall productivity of an industrial plant for the production of ethyl benzene is represented by the deactivation rate of the catalyst which is normally higher for the transalkylation step than for the alkylation step.

This is again due to the higher operating temperature which favours progressive condensation reactions of the aromatic rings responsible for the formation of coke, and also to the higher quantity of heavy compounds already present in the feeding to the transalkylation step, which also contribute to a more rapid formation of coke precursor impurities. Some of the problems described above have been solved, for example, as specified in U.S. Pat. No. 5,177,285, by means of a process for the production of ethyl benzene characterized in that the concentration of water at the inlet of the alkylation section is much higher than the concentration of water at the inlet of the transalkylation section and where, in both alkylation and transalkylation sections, a zeolitic catalyst is used, preferably a catalyst based on zeolite Y generally bound with alumina. It is known in fact that the catalytic activity of zeolites is generally depressed due to the presence of water, it is therefore convenient to have a less active catalyst in the alkylation section, where the main reaction is kinetically and thermodynamically favoured, in order to reduce the formation of by-products and impurities, and a more active catalyst in the transalkylation section, where the main reaction is kinetically and thermodynamically less favoured, in order to have the highest possible conversions of diethyl benzenes and triethyl benzenes and consequently reduce their non-converted quantity to be subjected to recirculation to the transalkylation reactor itself. The exploitation of a catalyst made more active by the use of particular reaction conditions, suitable for increasing its activity, allows the transalkylation reactor to be run at relatively lower temperatures. The reduction in the concentration of water is naturally obtained with the disadvantage of greater energy costs to reduce the water to concentrations lower than 100 ppm in the stream at the inlet of the transalkylation section.

A process for the production of ethyl benzene in which the catalyst used in the transalkylation section consists of a zeolite with larger pore dimensions with respect to the zeolite forming the catalyst used in the alkylation section, is described in U.S. Pat. No. 6,268,542. The catalyst used in the alkylation section preferably consists of a silicalite, belonging to the class of small-pore zeolites, in a monoclinic form, whereas the catalyst used in the transalkylation section consists of zeolite Y.

Also in this case, the specificity of the transalkylation reaction of polyethyl benzenes with respect to the alkylation reaction of benzene with ethylene, is evident.

The catalytic compositions of the present invention solve the problem of finding a specific catalyst for the transalkylation section, capable of high selectivities and of operating at lower operating temperatures, producing a high yield and overall productivity of transalkylation plants, in particular those for the industrial production of ethyl benzene.

A further object of the present invention therefore relates to a process for the transalkylation of aromatic hydrocarbons with one or more polyalkylated aromatic hydrocarbons catalysed by a catalytic composition comprising a zeolite having a crystalline structure with openings consisting of 12 tetrahedra (large-pore zeolites) and γ-alumina, as inorganic binder, said composition being characterized by a pore volume, obtained by adding the mesoporosity and the macroporosity fractions present in the catalytic composition, higher than or equal to 0.7 cc/g, wherein at least 30% of said volume consists of pores having a diameter greater than 100 nanometers.

Catalytic compositions containing zeolite Y in acidic form are preferably used.

The aromatic hydrocarbon is preferably benzene. The polyalkylated aromatic hydrocarbon is preferably selected from diethyl benzene, and optionally triethyl benzene, and di-isopropyl benzene, and optionally tri-isopropyl benzene. The transalkylation of benzene with diethyl benzene and optionally triethyl benzene, to give ethyl benzene is particularly preferred.

The transalkylation reaction should be carried out under such conditions as to at least partially take place in liquid phase and preferably under such conditions as to substantially take place in liquid phase. It is preferably carried out at a temperature ranging from 150 to 300° C., at a pressure ranging from 20 to 50 atms and a space velocity (WHSV) ranging from 0.5 to 10 hours$^{-1}$. The molar ratio between aromatic hydrocarbon and the sum of the polyalkylated aromatic hydrocarbons in the feeding mixture to the transalkylation reaction can vary from 1 to 40, preferably from 3 to 30. The catalytic composition, object of the present invention, is used in all types of reactors in which the catalyst can be arranged in a fixed bed and is particularly used in chamber reactors having one or more fixed beds of catalyst.

According to a further aspect of the present invention, the transalkylation activity of the catalyst, object of the present invention, can be suitably used for maximizing the production of a mono-alkylated product in the reaction of aromatics with light olefins, and in particular benzene with ethylene to give ethyl benzene. According to this particular aspect of the present invention, the product obtained in the alkylation reaction of aromatics with light olefins is separated into an aromatic hydrocarbon fraction, a mono-alkylated aromatic hydrocarbon fraction, a fraction of polyalkylated aromatic hydrocarbons, preferably prevalently comprising dialkylated aromatics, and a last fraction of heavy aromatic hydrocarbons.

The fraction of polyalkylated aromatic hydrocarbons, preferably prevalently comprising dialkylated aromatic hydrocarbons, is fed, together with an aromatic hydrocarbon, to a specific reactor, in the presence of the catalyst object of the present invention.

A further aspect of the present invention therefore relates to a process for preparing mono-alkylated aromatic hydrocarbons, which comprises:

a) putting an aromatic hydrocarbon in contact, in the presence of an acidic catalyst, with a $C_2$-$C_4$ olefin, under alkylation conditions which are such that the reaction takes place at least partially in liquid phase, b) separating the product obtained into a fraction containing an aromatic hydrocarbon, a fraction containing a mono-alkylated aromatic hydrocarbon, a fraction containing polyalkylated aromatic hydrocarbons, preferably prevalently containing dialkylated aromatic hydrocarbons, and a fraction of heavy aromatic hydrocarbons, c) putting the fraction containing polyalkylated aromatic hydrocarbons, preferably prevalently containing dialkylated products, in contact with an aromatic hydrocarbon, in the presence of the catalyst, object of the present invention, under transalkylation conditions which are such that the reaction takes place at least partially in liquid phase.

In the alkylation step a), a solid acidic catalyst is preferably used, containing a zeolite of the large-pore class. Zeolites preferably used in the catalytic composition used in the alkylation step are beta zeolite and zeolite Y. Beta zeolite is preferably used, as described in EP 432814. Even more preferably, the alkylation step is carried out according to EP 687500 or EP 847802 in which a catalytic composition is used, containing beta zeolite bound with an inorganic binder, characterized by particular porosity and pore volume characteristics.

The olefin which is preferably used in the alkylation step is selected from ethylene and propylene, and is even more preferably ethylene. The aromatic hydrocarbon used in the alkylation step is preferably benzene. A particularly preferred aspect is that benzene and ethylene are put in contact with each other in the alkylation step (a) in the presence of beta zeolite.

When the alkylation product is obtained from the alkylation reaction of benzene with ethylene, in step (b) the first fraction contains benzene, the second contains ethyl benzene, the third preferably prevalently consists of diethyl benzene and the last fraction consists of a mixture of heavy hydrocarbons having a boiling point greater than or equal to 260° C.

The third fraction, prevalently consisting of diethyl benzene, is put in contact, in step (c), with benzene, in the presence of the catalyst of the present invention, preferably containing zeolite Y, under transalkylation conditions, in at least partially liquid phase.

The fraction of polyalkylated products, in particular diethyl benzenes, fed to step (c) may also contain the unrecoverable by-products, described above, called Flux oil, preferably in a limited quantity and not higher than 0.1% by weight with respect to the total weight of the fed mixture, consisting of polyalkylated products and the aromatic hydrocarbon. The polyalkylated fraction, in particular diethyl benzenes, fed to step (c) may also contain variable quantities of butyl benzenes, up to a maximum of 2% by weight with respect to the total weight of the fed mixture, consisting of polyalkylated products and the aromatic hydrocarbon.

EXAMPLE 1

260 g of zeolite Y CBV 712 in powder form, produced and supplied by Zeolyst, and 278 g of p-bohemite Versal V-250 in powder form, produced and supplied by Laroche, are charged into a high-speed mixer (turbo-mixer), equipped with ploughs of the type indicated in FIG. 1 (of MIX S.r.l.—Modena—Italy).

The powders are dry-mixed for 60 minutes at a rate equal to 1000 rpm. At the end of the dry-mixing of the powders, 310 cc of an aqueous solution at 0.5% w/w of glacial acetic acid are added through a spray nozzle connected with the mixing chamber. The acetic solution is added at an approximately constant rate in about 36 minutes, during which the rate of the mixer is equal to 400 rpm. At the end of the addition of the acetic solution, a further mixing of the mixture present inside the mixer is effected, maintaining the selected rate of 400 rpm constant, for a further 12 minutes.

Figure 2:
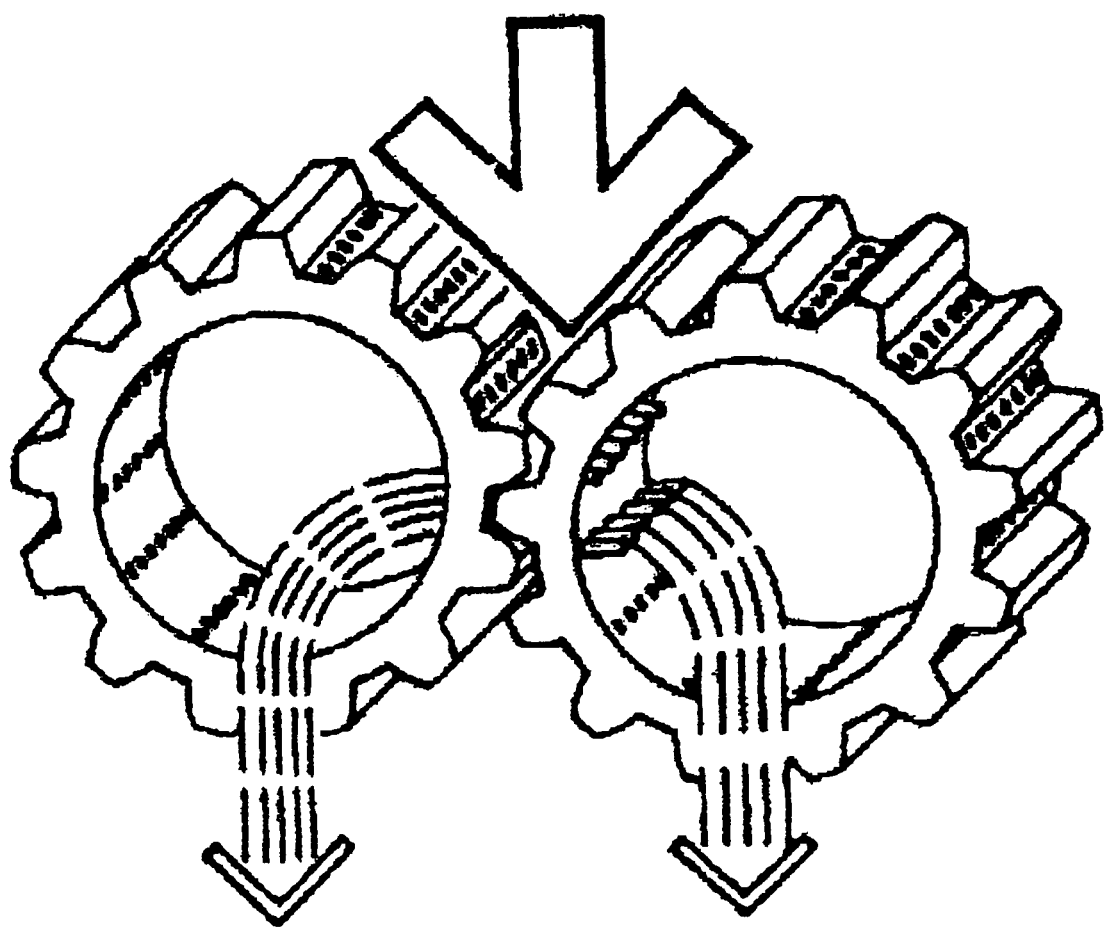
FIG. 2 shows a gear press extruder which may be used in a process of the invention.

The product thus obtained is discharged and submitted to an extrusion process with a gear press extruder, of which a detail is shown in FIG. 2, taken from Preparation of Solid Catalysts, page 585, edited by G. Ertl, H. Knozinger, J. Weitkamp, WILEY-VCH Publishing. At the end of the extrusion, the product thus obtained in the form of regular cylinders is placed in a ventilated oven at 25° C. for 48 hours. At the end of the drying, the product obtained is then placed in a muffle to calcinate, in an atmosphere of air, with the following temperature ramp:

from room temperature to 120° C. in 360 minutes, isotherm at 120° C. for 120 minutes, from 120° C. to 350° C. in 360 minutes, isotherm at 350° C. for 240 minutes, from 350° C. to 550° C. in 240 minutes, isotherm at 550° C. for 480 minutes.

The finished catalyst is in the form of regular cylinders with a length approximately equal to 7 mm±1 mm and with a diameter equal to 2.1 mm±0.1 mm.

Once the calcination has been completed and the product has cooled, the extra-zeolitic and mechanical characteristics of the catalysts are measured.

Figure 3:
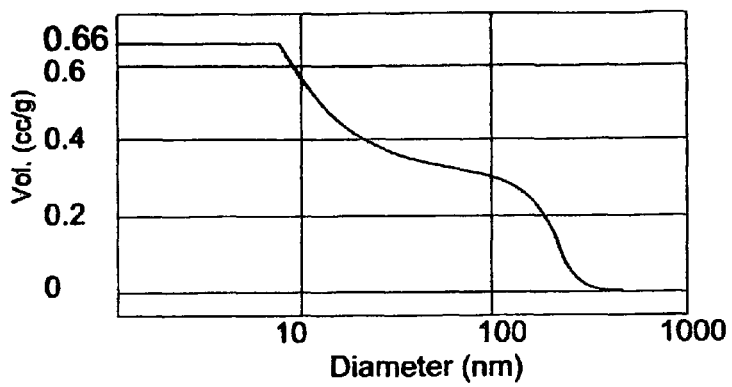
FIG. 3 shows the pore size distribution of an embodiment of the catalytic composition of the invention.
Figure 3:
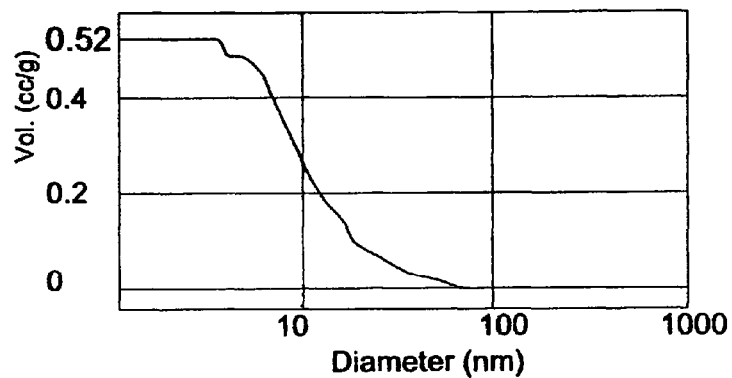
Figure 3:
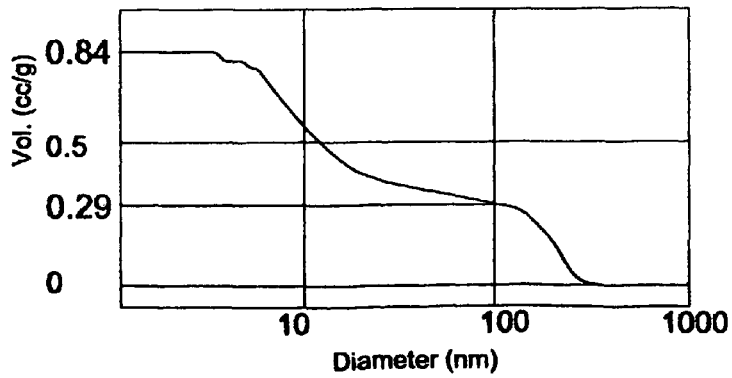

FIG. 3 indicates the pore size distributions (PSD) obtained by means of mercury porosimetry at the top, nitrogen porosimetry at the temperature of liquid nitrogen in the centre and the total extra-zeolitic pore size distribution, obtained by joining the previous two, at the bottom, wherein the porosity of the zeolite itself is not indicated. In particular, in abscissa there is the pore diameter in nanometers (diameter) and in the ordinate the pore volume in cc/g (Vol.). The determination of the pore size distributions was effected using a Carlo Erba Porosimeter 2000® for the mercury porosimetries and an ASAP 2010 Micromeritics® for the physical adsorption of nitrogen at the temperature of liquid nitrogen.

The total extra-zeolitic porosity proves to be equal to 0.84 cc/g with a fraction of said extra-zeolitic porosity having a pore diameter greater than 100 nanometers equal to 34.5% (0.29 cc/g/0.84 cc/g*100). The crushing strength measured according to the method ASTM D6175-98 proves to be equal to 2.1 kg/mm. The apparent density is equal to 0.46 g/cc.

The product consists of 49.99% by weight of γ-alumina and 50.01% by weight of zeolite Y on the basis of the weight loss at 550° C. measured on the starting components.

XRD analysis effected on the catalyst confirms the sole presence of the faujasite phases (zeolite Y) and γ-alumina.

Figure 4:
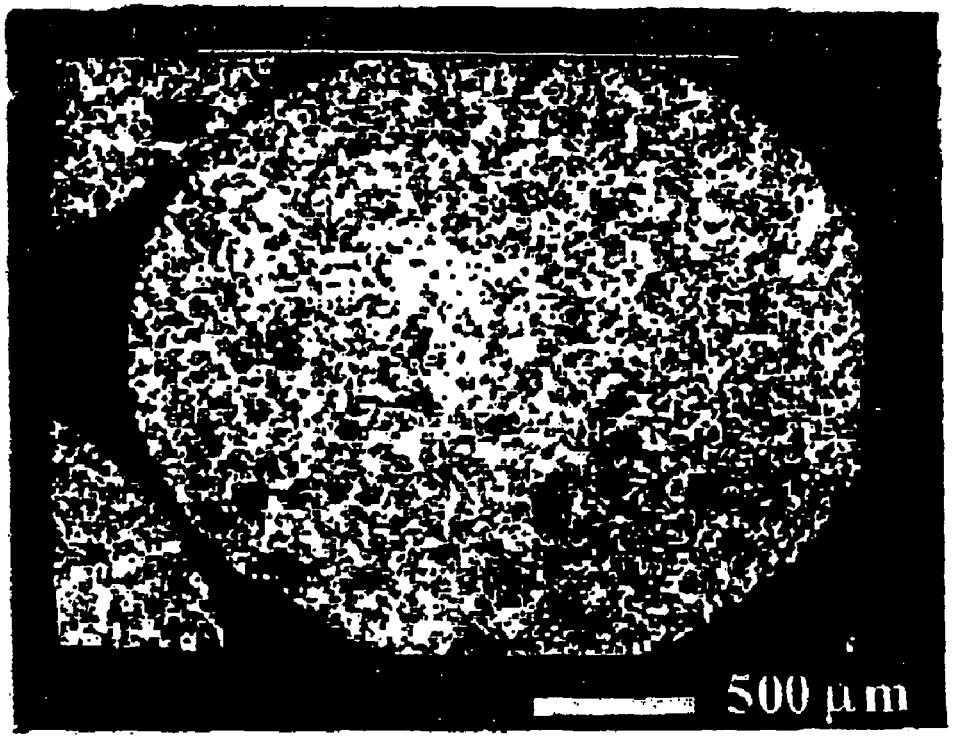
FIG. 4 shows an SEM image for Al and Si elements in an embodiment of the catalytic composition of the invention.
Figure 4:
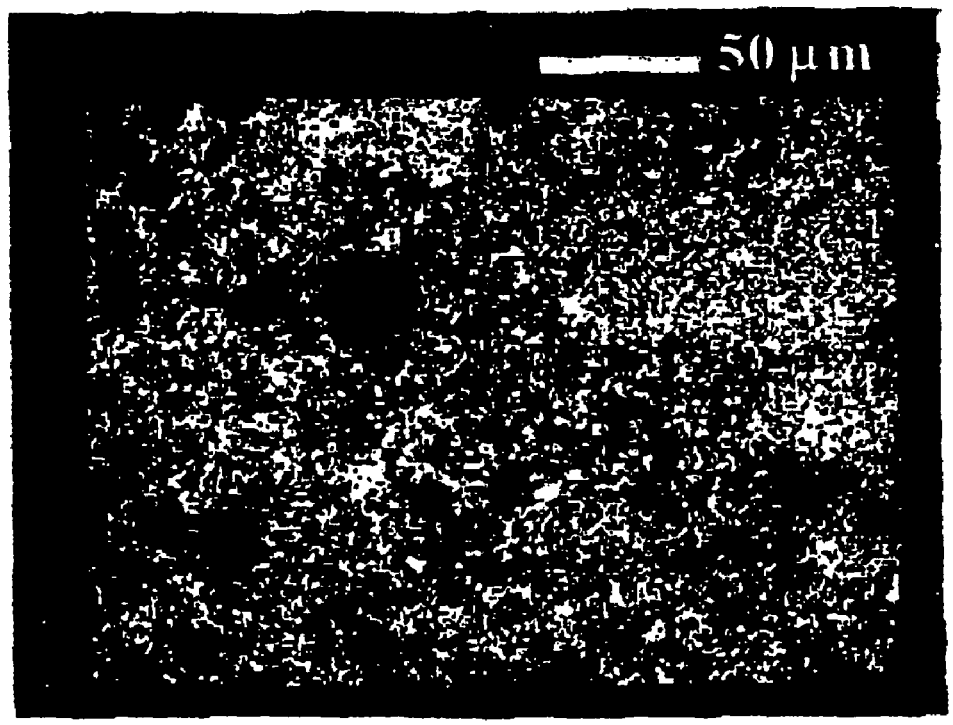

FIG. 4 also shows a series of photographs obtained by means of SEM microscopy and EDS probe for the mapping of the elements Al and Si, which can be assimilated to the alumina binder and zeolite forming the catalyst, respectively. The Si is shown with a dark shade, whereas the Al is indicated with a light shade. Morphological tests were carried out by means of Scanning Electronic Microscopy (SEM), using a Jeol JSM-5400LV scanning electronic microscope equipped with a EDAX JSM-5300 microprobe for the EDS (Energy Dispersive Spectroscopy) analysis. The samples were englobed in epoxy resin and subsequently polished until transversal sections of the cylinders were obtained.

FIG. 4 shows the distribution of the alumina and zeolite phases in the catalyst prepared according to the present Example 1, at different enlargements. The first upper photo, obtained at smaller enlargements than the second, shows an apparently homogeneous phase distribution. In the second photo below, obtained at greater enlargements with respect to the first, a rather heterogeneous phase distribution can be observed, on the contrary, characterized by alumina and zeolite particles with varying dimensions, sometimes differing by at least one order of magnitude with respect to the average particle sizes.

EXAMPLE 2

A catalytic test is effected in the transalkylation reaction of benzene with polyethyl benzenes. The reactor used for the catalytic test is of the Berty type, consisting of a reaction chamber having a capacity of 250 cc in which there is a 50 cc basket into which the catalyst prepared as described in Example 1, is charged. The reactor head is positioned in the upper part of the reaction chamber, which supports an impeller which rotates by means of a magnetic joint. The reactor is equipped with a temperature and pressure regulation system.

The feeding mixture, before the reactor inlet, is passed through a column of alumina in order to reduce the quantity of water contained therein to below 50 ppm and is then fed in continuous to the reactor. The test is carried out under the following conditions:
reaction temperature equal to 210° C., reaction pressure equal to 50 bar, space velocity expressed as WHSV equal to 4 hours$^{-1}$, molar ratio [benzene]/[total polyethyl benzenes] equal to 20. The molar ratio between benzene and total polyethyl benzenes corresponds to the following weight concentrations with respect to the total weight of the mixture fed: diethyl benzenes equal to 6.9%, triethyl benzenes equal to 0.04%, butyl benzenes equal to 1%. The overall concentration of the biphenyl ethanes is lower than 20 ppm by weight.

The effluent from the reactor is collected in a tank and analyzed by means of gaschromatography using an HP 5890 Series 2 instrument equipped with a capillary column with the stationary phase Carbovax 20M and detector of the flame ionization (FID) type.

After activating the reactor under the above conditions, two samplings of the reaction effluent were effected together with the relative Gaschromatographic analyses.

Table 1 indicates the results relating to the two samples.

With a productivity equal to about 24 g of ethyl benzene per g of catalyst, the conversion of the polyethyl benzenes and molar yield to ethyl benzene with respect to the polyethyl benzenes converted, were equal to 80.1% and 71.4% respectively.

With a productivity equal to 145 g of ethyl benzene per g of catalyst, the conversion of the polyethyl benzenes and molar yield to ethyl benzene with respect to the polyethyl benzenes converted were equal to 78.9% and 69.1% respectively.

The decrease in the yield to ethyl benzene was therefore equal to 2.3% as an absolute value and equal to 0.019% as an absolute value per productivity unit (yield variation/productivity variation).

EXAMPLE 3-COMPARATIVE 260 gr of zeolite Y CBV 712 in powder form, produced and supplied by Zeolyst, and 278 gr of p-bohemite Versal V-250 in powder form, produced and supplied by Laroche, are charged into a "Z Blade"-type mixer manufactured by Erweka.

The powders are dry-mixed for 70 minutes at a rate equal to 45 rpm. At the end of the dry-mixing of the powders, 310 cc of an aqueous solution at 0.3% w/w of glacial acetic acid are added. The acetic solution is added at an approximately constant rate in about 50 minutes, during which the rate of the mixer is equal to 45 rpm. At the end of the addition of the acetic solution, a further mixing of the mixture present inside the mixer is effected, maintaining the selected rate of 45 rpm, for a further 30 minutes constant.

The product thus obtained is discharged and submitted to an extrusion process with a gear press extruder, of the type shown in FIG. 2. At the end of the extrusion, the product thus obtained in the form of regular cylinders is placed in a ventilated oven at 25° C. for 24 hours.

At the end of the drying, the product obtained is then placed in a muffle oven to calcinate, in an atmosphere of air, with the following temperature slope:
from room temperature to 120° C. in 360 minutes, isotherm at 120° C. for 120 minutes, from 120° C. to 350° C. in 360 minutes, isotherm at 350° C. for 240 minutes, from 350° C. to 550° C. in 240 minutes, isotherm at 550° C. for 480 minutes.

The catalyst is in the form of regular cylinders with a length approximately equal to 7 mm±1 mm and with a diameter equal to 2.1 mm±0.1 mm.

Once the calcination has been completed and the product has cooled, the extra-zeolitic and mechanical characteristics of the catalysts are measured.

Figure 5:
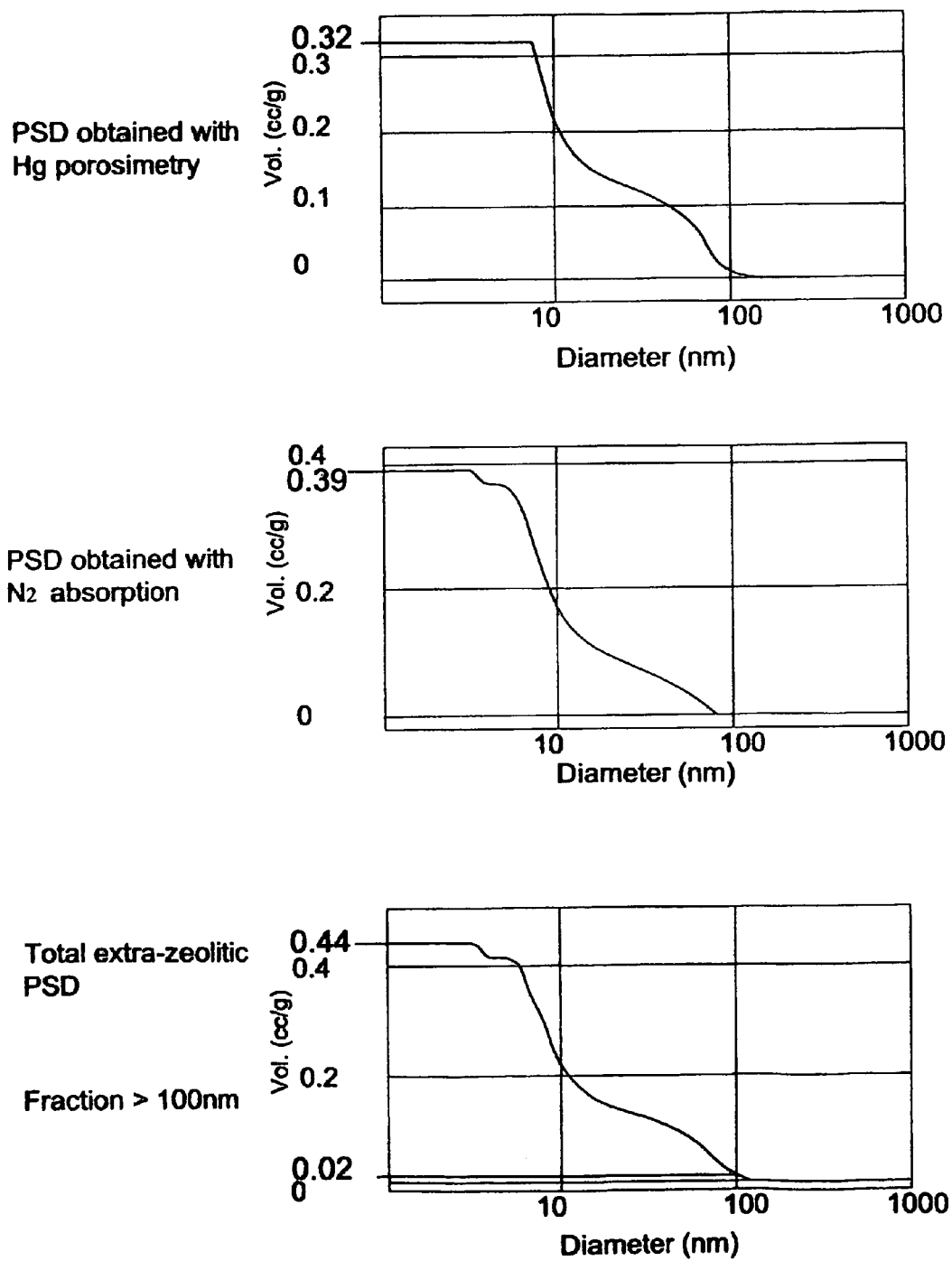
FIG. 5 shows the pore size distribution in another embodiment of the invention.

FIG. 5 indicates the pore size distributions (PSD) obtained by means of mercury porosimetry at the top, nitrogen porosimetry at the temperature of liquid nitrogen in the centre and the total extra-zeolitic pore size distribution, obtained by joining the previous two, at the bottom, wherein the porosity of the zeolite itself is not indicated. In particular, in abscissa there is the pore diameter in nanometers (diameter) and in the ordinate the pore volume in cc/g (Vol.).

The total extra-zeolitic porosity proves to be equal to 0.44 cc/g with a fraction of said extra-zeolitic porosity having a pore diameter greater than 100 nanometers equal to 0.04% (0.02 cc/g/0.44 cc/g*100). The crushing strength measured according to the method ASTM D6175-98 proves to be equal to 1.4 kg/mm. The apparent density is equal to 0.74 g/cc.

The product consists of 49.99% by weight of γ-alumina and 50.01% by weight of zeolite Y on the basis of the weight loss at 550° C. measured on the starting components.

XRD analysis effected on the catalyst confirms the sole presence of the zeolite Y and γ-alumina phases.

Figure 6:
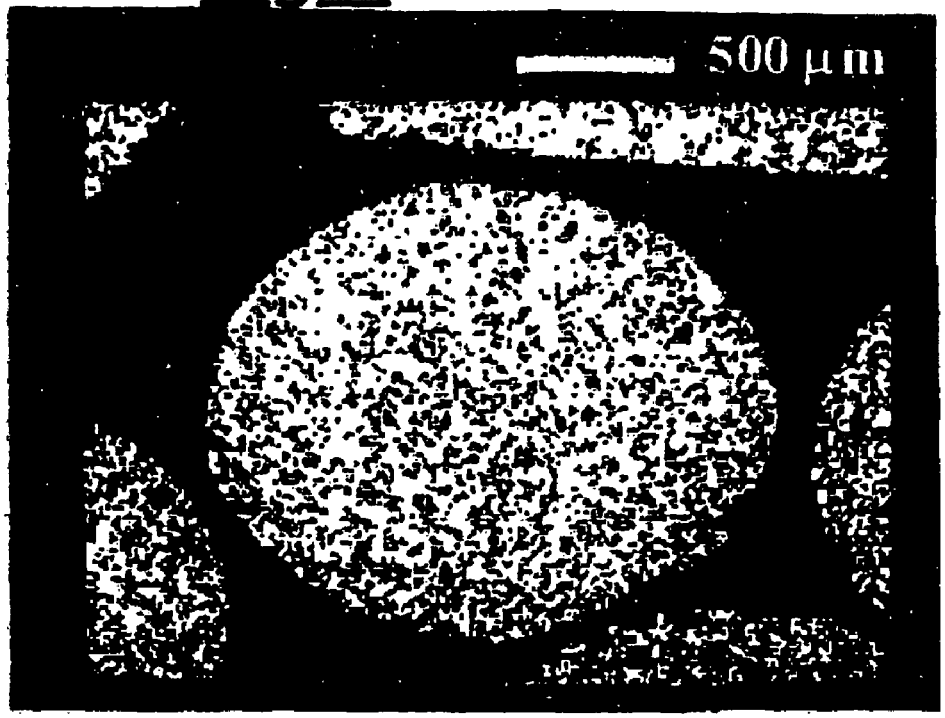
FIG. 6 shows SEM micrographs of the catalytic composition of an embodiment of the invention indicating elements Al and Si.
Figure 6:
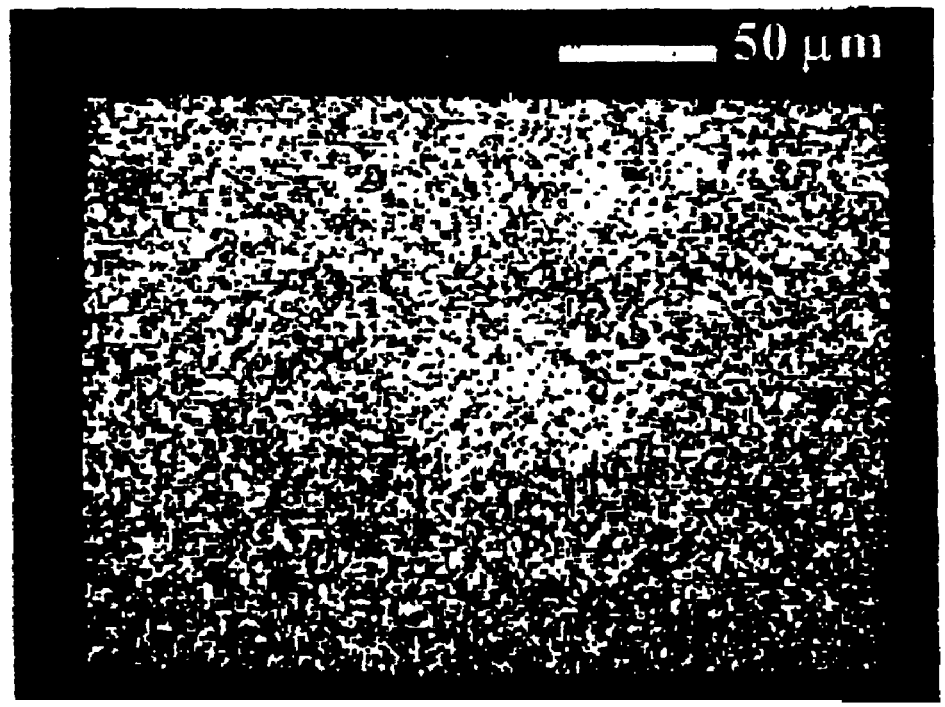

FIG. 6 also shows a series of photographs obtained by means of SEM microscopy and EDS probe for the mapping of the elements Al and Si, which can be assimilated to the alumina binder and zeolite forming the catalyst, respectively. The Si is shown with a dark shade, whereas the Al is indicated with a light shade. Morphological tests were carried out by means of scanning electronic microscopy (SEM), using a Jeol JSM-5400LV scanning electronic microscope equipped with a EDAX JSM-5300 microprobe for the EDS (Energy Dispersive Spectroscopy) analysis. The samples were englobed in epoxy resin and subsequently polished until transversal sections of the cylinders were obtained.

FIG. 6 shows the distribution of the alumina and zeolite phases in the catalyst prepared according to the present Example 3, at different enlargements. A homogeneous distribution of the phases can be observed in both photos, with only an occasional presence of particles having higher dimensions. On comparing the two lower photos (at greater enlargements) of FIG. 6 and FIG. 4, the latter referring to the catalyst, object of the present invention, the different particle size distribution of the zeolite and alumina particles from both a relative and absolute point of view, is evident.

The particle size in FIG. 6 is in fact extremely reduced with respect to the particle size of FIG. 4 and is also characterized by a greater homogeneity in the two components.

EXAMPLE 4-COMPARATIVE

A catalytic test is effected in the transalkylation reaction of benzene with polyethyl benzenes. The equipment used and test operating procedures are the same as those of Example 2. The catalyst used is that prepared in Example 3. Table 1 indicates the results relating to the two samples.

With a productivity equal to about 24 g of ethyl benzene per g of catalyst, the conversion of the polyethyl benzenes and molar yield to ethyl benzene with respect to the polyethyl benzenes converted were equal to 78.3% and 71.1% respectively.

With a productivity equal to 145 g of ethyl benzene per g of catalyst, the conversion of the polyethyl benzenes and molar yield to ethyl benzene with respect to the polyethyl benzenes converted were equal to 73.9% and 61.8% respectively.

The decrease in the yield to ethyl benzene was therefore equal to 9.3% as an absolute value and equal to 0.077% as an absolute value per productivity unit (yield variation/productivity variation).

The decrease in yield to ethyl benzene was, in this case, higher than the decrease in yield registered in Example 2 when the catalyst used is a catalyst according to the present invention prepared as described in Example 1.

TABLE 1

|  | Productivity (g ethyl benzene/g catalyst) | |
|---|---|---|
|  | 24 | 145 |
| Example 2 |  |  |
| Polyethyl benzenes conversion (%) | 80.1 | 78.9 |
| Yield to ethyl benzene (molar %) | 71.4 | 69.1 |
| Yield variation/productivity variation [%/(g/g)] | — | −0.019 |
| Example 4 |  |  |
| Polyethyl benzenes conversion (%) | 78.3 | 73.9 |
| Yield to ethyl benzene (molar %) | 71.1 | 61.8 |
| Yield variation/productivity variation [%/(g/g)] | — | −0.077 |

The invention claimed is:

1. A transalkylation process, comprising:
   contacting an aromatic hydrocarbon mixture comprising one or more polyalkylated aromatic hydrocarbons and a non-alkylated aromatic hydrocarbon with a catalytic composition, to thereby transalkylate, in the liquid phase, one or more alkyl groups from the polyalkylated aromatic hydrocarbons to the non-alkylated aromatic hydrocarbon and form a mono-alkylated aromatic hydrocarbon,
   wherein the catalytic composition, comprises:
      a zeolite and an inorganic binder,
         wherein the zeolite is zeolite Y having a $SiO_2/Al_2O_3$ molar ratio of from 10 to 20, and the binder is γ-alumina,
         wherein said catalytic composition has a pore volume, obtained by adding the mesoporosity and macroporosity fractions present in the catalytic composition, of greater than or equal to 0.7 cc/g,
   wherein at least 30% of said pore volume consists of pores with a diameter greater than 100 nanometers.

2. The process according to claim 1, further comprising:
   before the contacting, contacting an aromatic hydrocarbon, in the presence of the catalytic composition, with a $C_2$-$C_4$ olefin, under alkylation conditions to form an alkylation aromatic hydrocarbon mixture,
   separating the alkylation hydrocarbon aromatic mixture into a first fraction comprising an aromatic hydrocarbon, a second fraction comprising a mono-alkylated aromatic hydrocarbon, a third fraction containing the polyalkylated aromatic hydrocarbon and a fourth fraction comprising heavy aromatic hydrocarbons.

3. The process according to claim 1, wherein the catalytic composition comprises zeolite Y in acidic form.

4. The process according to claim 3, wherein the olefin is at least one of ethylene and propylene.

5. The process according to claim 3, wherein the olefin is ethylene.

6. The process according to claim 1, wherein the non-alkylated aromatic hydrocarbon is benzene.

7. The process according to claim 1, wherein the hydrocarbon mixture consists of the polyalkylated aromatic hydrocarbons and the non-alkylated aromatic hydrocarbon.

8. The process according to claim 1, wherein the hydrocarbon mixture is free of olefin.

9. The process of claim 1, wherein the catalytic composition has a crushing strength equal to or higher than 1.7 kg/mm.

10. The process of claim 1, wherein the catalytic composition has an apparent density not higher than 0.5 cc/g.

11. The process of claim 1, wherein the catalytic composition is in the form of particles having a diameter not lower than 1.8 mm.

12. The process of claim 11, wherein the catalytic composition is in the form of particles having a diameter not lower than 2.0 mm.

13. The process of claim 1, wherein the catalytic composition is in the form of cylindrical pellets.

14. The process of claim 1, wherein the zeolite Y and the binder are in a weight ratio greater than 1:1 and lower than or equal to 4:1.

15. The process of claim 1, wherein the zeolite Y has a $SiO_2/Al_2O_3$ molar ratio ranging from 11 to 17.

16. A process for the transalkylation of aromatic hydrocarbons, comprising:
contacting an aromatic hydrocarbon with one or more polyalkylated aromatic hydrocarbons in the presence of a catalytic composition operating so that the reaction takes place at least partially in liquid phase,
wherein the catalytic composition, comprises:
a zeolite and an inorganic binder,
wherein the zeolite is zeolite Y having a $SiO_2/Al_2O_3$ molar ratio of from 10 to 20, and the binder is γ-alumina,
wherein said catalytic composition has a pore volume, obtained by adding the mesoporosity and macroporosity fractions present in the catalytic composition, of greater than or equal to 0.7 cc/g,
wherein at least 30% of said pore volume consists of pores with a diameter greater than 100 nanometers.

17. The process according to claim 16, wherein the catalytic composition contains zeolite Y in acidic form.

18. The process of claim 16, carried out at a temperature ranging from 150 to 300° C., a pressure ranging from 20 to 50 atms and a WHSV ranging from 0.5 to 10 hours$^{-1}$.

19. The process of claim 16, wherein the molar ratio between the aromatic hydrocarbon and the sum of the polyalkylated aromatic hydrocarbons varies from 1 to 40.

20. The process of claim 19, wherein the molar ratio between the aromatic hydrocarbon and polyalkylated aromatic hydrocarbons varies from 3 to 30.

21. The process of claim 16, wherein the aromatic hydrocarbon is benzene.

22. The process of claim 16, wherein the polyalkylated aromatic hydrocarbon is diethyl benzene, optionally mixed with triethyl benzene, or di-isopropyl benzene, optionally mixed with tri-isopropyl benzene.

23. The process of claim 22, wherein the aromatic hydrocarbon is benzene and the polyalkylated aromatic hydrocarbon is diethyl benzene and optionally triethyl benzene.

24. A process for preparing mono-alkylated aromatic hydrocarbons, comprising:
a) contacting an aromatic hydrocarbon, in the presence of an acidic catalyst, with a $C_2$-$C_4$ olefin, under alkylation conditions which are such that the reaction takes place at least partially in liquid phase,
b) separating the product obtained into a fraction containing an aromatic hydrocarbon, a fraction containing a mono-alkylated aromatic hydrocarbon, a fraction containing polyalkylated aromatic hydrocarbons, and a fraction of heavy aromatic hydrocarbons, and
c) contacting the fraction containing polyalkylated aromatic hydrocarbons in contact with an aromatic hydrocarbon, in the presence of a catalytic composition under transalkylation conditions which are such that the reaction takes place at least partially in liquid phase,
wherein the catalytic composition, comprises:
a zeolite and an inorganic binder,
wherein the zeolite is zeolite Y having a $SiO_2/Al_2O_3$ molar ratio of from 10 to 20, and the binder is γ-alumina,
wherein said catalytic composition has a pore volume, obtained by adding the mesoporosity and macroporosity fractions present in the catalytic composition, of greater than or equal to 0.7 cc/g,
wherein at least 30% of said pore volume consists of pores with a diameter greater than 100 nanometers.

25. The process according to claim 24, wherein in step (c) the catalytic composition contains zeolite Y in acidic form.

26. The process of claim 24, wherein in step (a) the olefin is ethylene or propylene.

27. The process of claim 26, wherein the olefin is ethylene.

28. The process of claim 24, wherein in step (a) the aromatic hydrocarbon is benzene.

29. The process of claim 24, wherein in step (a) the catalyst contains beta zeolite, the olefin is ethylene and the aromatic hydrocarbon is benzene.

30. The process of claim 24, wherein in step (b) the fraction of polyalkylated aromatic hydrocarbons prevalently contains dialkylated aromatic hydrocarbons.

31. The process of claim 24, wherein in step (a) the hydrocarbon is benzene and the olefin is ethylene, in step (b) the first fraction contains benzene, the second fraction contains ethyl benzene, the third fraction prevalently contains diethyl benzene and the last fraction consists of a mixture of heavy hydrocarbons having a boiling point equal to or higher than 260° C., and in step (c) the third fraction is put in contact with benzene.

32. The process of claim 24, wherein the fraction of polyalkylated products fed to step (c) contains a mixture of Flux oil.

33. The process of claim 24, wherein the fraction of polyalkylated products fed to step (c) contains butyl benzenes in a quantity not higher than 2% by weight with respect to the total weight of the mixture fed.

34. The process of claim 24, wherein the catalytic composition has a crushing strength of 2.1 kg/mm or greater according to ASTM D6175-98.

35. The process of claim 24, wherein the zeolite Y is dispersed in the inorganic binder and the inorganic binder is γ-alumina.

36. The process of claim 24, wherein in step (a) the acidic catalyst is a catalytic composition containing a zeolite.

37. The process of claim 24, wherein in step (a) the acidic catalyst is a catalytic composition containing a zeolite.

38. The process of claim 36, wherein the zeolite is beta zeolite.

39. The process of claim 38, wherein the zeolite is beta zeolite.

40. The process of claim 31, wherein the acidic catalyst in step (a) is beta zeolite.

* * * * *